(12) United States Patent
Tezuka et al.

(10) Patent No.: US 8,880,136 B2
(45) Date of Patent: Nov. 4, 2014

(54) CALIBRATION METHOD FOR CALIBRATING AN INSTRUMENT FOR MEASURING BIOGENIC SUBSTANCE, USING NEAR-INFRARED SPECTRAL SPECTROSCOPY

(75) Inventors: Shin-ichiro Tezuka, Musashino (JP); Hitoshi Hara, Musashino (JP)

(73) Assignee: Yokogawa Electric Corporation, Tokyo (JP)

( * ) Notice: Subject to any disclaimer, the term of this patent is extended or adjusted under 35 U.S.C. 154(b) by 488 days.

(21) Appl. No.: 13/184,259

(22) Filed: Jul. 15, 2011

(65) Prior Publication Data
US 2012/0016214 A1  Jan. 19, 2012

(30) Foreign Application Priority Data
Jul. 15, 2010  (JP) ................. 2010-160533

(51) Int. Cl.
  *A61B 5/1455* (2006.01)
  *G01N 21/35* (2014.01)
  *G01N 21/27* (2006.01)
(52) U.S. Cl.
  CPC ............ *G01N 21/274* (2013.01); *A61B 5/1455* (2013.01); *G01N 21/359* (2013.01); *A61B 2560/0223* (2013.01)
  USPC ......................................... 600/316; 600/310
(58) Field of Classification Search
  USPC ................ 600/310, 316, 322; 250/252.1
  See application file for complete search history.

(56) References Cited

U.S. PATENT DOCUMENTS

| | | | | |
|---|---|---|---|---|
| 5,068,536 A | * | 11/1991 | Rosenthal | ........................ 600/316 |
| 7,072,701 B2 | * | 7/2006 | Chen et al. | ..................... 600/331 |
| 2006/0063991 A1 | | 3/2006 | Yu et al. | |

FOREIGN PATENT DOCUMENTS

| | | |
|---|---|---|
| DE | 102006036920 B3 | 11/2007 |
| JP | 10-155775 A | 6/1998 |
| JP | 10-216112 A | 8/1998 |
| JP | 10-325794 A | 12/1998 |
| JP | 11-155840 A | 6/1999 |
| JP | 2008-301944 A | 12/2008 |

OTHER PUBLICATIONS

K. Maruo, et al., "Development State of Optical Blood Glucose Value Measuring System", Medical Appliance, Japanese Society of Medical Instrumentation, Aug. 2003, pp. 406-414, vol. 73, No. 8.
Extended European Search Report dated Aug. 23, 2012, issued by the European Patent Office in corresponding European Application No. 11174066.8.

* cited by examiner

*Primary Examiner* — Eric Winakur
(74) *Attorney, Agent, or Firm* — Sughrue Mion, PLLC

(57) ABSTRACT

A simple calibration method for calibrating an instrument for measuring a biogenic substance, using near-infrared spectral spectroscopy is realized. The calibration method comprises (1) the step of measuring a specific substance of a biological object with the use of an instrument for measuring a biogenic substance, using a confocal optical system, (2) the step of using an instrument for measuring a biogenic substance, using near-infrared spectral spectroscopy, thereby measuring a specific substance in the same region of the biological object, (3) the step of comparing a measured value of the specific substance, measured in the step (1) with a measured value of the specific substance, measured in the step, and (4) the step of executing an operation in the step at least once after the elapse of predetermined time.

3 Claims, 5 Drawing Sheets

CALIBRATION METHOD FOR CALIBRATING AN INSTRUMENT FOR MEASURING BIOGENIC SUBSTANCE, USING NEAR-INFRARED SPECTRAL SPECTROSCOPY

This application claims priority from Japanese Patent Application No. 2010-160533, filed on Jul. 15, 2010, the entire contents of which are herein incorporated by reference.

BACKGROUND

1. Technical Field

The present invention relates to a calibration method for calibrating an instrument for measuring a biogenic substance, using near-infrared spectral spectroscopy, and in particular, to a non-infesting calibration method for calibrating an instrument for measuring a biogenic substance, using near-infrared spectral spectroscopy, by the use of an instrument for measuring a biogenic substance, using a confocal optical system, as a reference.

2. Related Art

In the case of measuring concentration of a blood component, such as blood glucose, and so forth, in the past, blood has been often actually collected from a human body by use of a syringe, or by piercing a fingertip, or an earlobe. In contrast, there have lately been proposed techniques (refer to Patent Documents 1 to 4, and Non-patent Document 1) whereby a biological object is irradiated with light instead of collecting blood through infestation of the biological object, carried out as in the past, and reflected light from the biological object, and light transmitted through the biological object are detected, thereby measuring concentration of a blood component as a measurement subject, and so forth on the basis of a degree of light absorbed (absorbance) by the biological object.

With the technique described in Non-patent Document 1, in particular, with skin tissues of a human body, comprising epidermal tissues a1, dermal tissues a2, and hypodermal tissues a3, as shown in FIG. 2, capillary vessels are not well developed inside the epidermal tissues a1, and the hypodermal tissues a3 is made up mainly of adipose tissues; in contrast, capillary vessels are well developed inside the tissues of the dermal tissues a2 present between the epidermal tissues a1, and the hypodermal tissues a3, and since glucose having high permeability undergoes permeation into tissues from within a blood vessel, it is presumed that there exists correlation between concentration of glucose in the dermal tissues a2, and a blood glucose value in blood.

Under such presumption, there has been proposed a near-infrared spectroscopic analysis whereby a probe P is butted against a skin, the probe P being made up of an optical fiber Fin for incident light, and an optical fiber Fdet for detection, the skin is irradiated with a near-infrared ray R emitted from the optical fiber Fin for incident light to cause the near-infrared ray R to be transmitted through the dermal tissues a2 before being detected by the optical fiber Fdet for detection, the concentration of glucose in the dermal tissues a2 is measured from absorbance of the near-infrared ray R, and a blood glucose value in blood is predicted on the basis of results of such a measurement.

Further, in Patent Document 1, there is described an instrument for measuring a biogenic substance, using a confocal optical system, as shown in FIG. 3. FIG. 3 is briefly explained about hereinafter.

The instrument 1 for measuring a biogenic substance is comprised of a confocal optical system 2 for collecting data on a biogenic substance of a biological object A, and a data analysis system 3 for analyzing the data obtained.

The confocal optical system 2 is provided with a placement board 21, on which a biological object A, such as, for example, an arm of a test subject, is placed. Provided above the biological object A is a laser 22 capable of emitting laser beams at two or more wavelengths, and in this case, use is made of a wavelength-variable laser.

A collimator lens 23 for turning a laser beam into parallel rays is disposed in the back stage of the laser 22, and a half mirror 24 having a tilt by approximately 45° against the optical axis is disposed in the back stage of the collimator lens 23, the laser beam being transmitted through the half mirror 24.

An objective lens 25 for converging the parallel rays that are turned from the laser beam emitted from the laser 22 is disposed in the back stage of the half mirror 24, the laser beam irradiating internal tissues of the biological object A.

Reflected light that is reflected by the internal tissues of the biological object A is refracted by the objective lens 25 to be turned into parallel rays to be subsequently reflected by the half mirror 24, whereupon an optical path thereof is converted by approximately 90°.

Disposed on a side of the half mirror 24 is a lens 26 for receiving the reflected light whose optical path is converted, and converging the same, and the light reflected by the half mirror 24 is converged at the position of a pinhole 27 provided on a side of the lens 26 to pass through the pinhole 27 before being received by a photodetector 28 made up of, for example, a photodiode.

The pinhole 27 can be configured in such a way as to enable a quantity of the reflected light passing therethrough to be adjusted by adoption of, for example, a configuration wherein the pinhole 27 is provided with a diaphragm, a plurality of pinholes are provided so as to be switched over among them, and so forth.

Current, and voltage, varying in intensity and magnitude, according to a quantity of the reflected light as received, are outputted as data signals, respectively, from the photodetector 28, and the data signals undergo an A/D conversion by the agency of an A/D converter 29 to be transmitted to the data analysis system 3 of the instrument 1 for measuring a biogenic substance.

As shown in FIG. 4, the data analysis system 3 is made up of a computer wherein a CPU 31, a ROM 32, a RAM 33, and an input/output interface 34 are connected to a bus 35. The CPU 31 reads various programs stored in the ROM 32, such as a program for data analysis, and so forth, to be expanded as appropriate on the RAM 33, thereby executing various processing.

In data analysis, the CPU 31 executes quantitative determination of the biogenic substance of the biological object A on the basis of a plurality of the data signals inputted from the photodetector 28 via the A/D converter 29, and the input/output interface 34 due to emission of the respective laser beams varying in wavelength, at two or more wavelengths.

More specifically, in the case of determining a blood glucose value, that is, the concentration of glucose in blood, since an analytical curve indicating a correlation between the concentration of glucose in blood, and absorbance of a laser beam, as shown in FIG. 5, is stored in the ROM 32, the CPU 31 executes the quantitative determination of the biogenic substance of the biological object A on the basis of the analytical curve.

RELATED ART LITERATURE

Patent Documents (Patent Document 1) JP2008301944 A
(Patent Document 2) JP10155775 A
(Patent Document 3) JP10216112 A
(Patent Document 4) JP10325794 A
(Patent Document 5) JP11155840 A
(Non-patent Document 1) "Development State of Optical Blood Glucose Value Measuring System", By K. Maruo, et al., Medical Appliance, Japan Institute of Medical Science, August 2003, Vol. 73, No. 7, p. 406-414

Now, with the technique described in Patent Document 1, mitigation in effects on the epidermal tissues a1, and the hypodermal tissues a3 among the skin tissues, can be expected to mitigate to an extent, however, since the near-infrared ray R falling on the skin tissues is transmitted through the epidermal tissues a1 to be subsequently transmitted through the dermal tissues a2, and passes through the epidermal tissues a1 again before being detected by the optical fiber Fdet for detection, this is hardly considered to represent the case where the concentration of glucose in the dermal tissues a2 is selectively detected.

Further, if an interval between the optical fiber for incident light, and the optical fiber for detection is fixed, this will render it impossible to cope with a personal difference in the skin tissues, such as thickness of the epidermal tissues a1, thickness of the dermal tissues a2, and so forth, thereby creating a factor responsible for an error.

Furthermore, with the instrument for measuring a biogenic substance, using near-infrared spectral spectroscopy, infestation measurement of a blood glucose value has been required at intervals of several hours in order to reconstruct an analytical curve.

In addition, there have existed problems with the instrument for measuring a biogenic substance, using the confocal optical system, as described in Patent Document 1, in that the number of components is large although measuring precision is high, skill as well as precision in positioning of optical components is required, and work for assembling takes time, resulting in high cost.

SUMMARY OF THE INVENTION

Exemplary embodiments of the present invention address the above disadvantages and other disadvantages not described above. However, the present invention is not required to overcome the disadvantages described above, and thus, an exemplary embodiment of the present invention may not overcome any disadvantages.

It is one of illustrative aspects of the present invention to calibrate an instrument for measuring a biogenic substance, using near-infrared spectral spectroscopy, with the use of an instrument for measuring a biogenic substance, using a confocal optical system, as a reference, thereby implementing a non-infesting and simple calibration method for calibrating the instrument for measuring a biogenic substance, using near-infrared spectral spectroscopy.

According to one or more illustrative aspects of the invention, there is provided a calibration method for calibrating an instrument for measuring a biogenic substance, using near-infrared spectral spectroscopy, the method comprising (1) the step of measuring a specific substance of a biological object with the use of an instrument for measuring a biogenic substance, using a confocal optical system, (2) the step of using an instrument for measuring a biogenic substance, using near-infrared spectral spectroscopy, thereby measuring a specific substance in the same region of the biological object that is measured with the use of the instrument for measuring a biogenic substance, using the confocal optical system, (3) the step of comparing a measured value of the specific substance, measured in the step (1) with the use of the instrument for measuring a biogenic substance, using the confocal optical system, with a measured value of the specific substance, measured in the step (2) with the use of the instrument for measuring a biogenic substance, using near-infrared spectral spectroscopy, and calibrating the measured value of the specific substance, measured with the use of the instrument for measuring a biogenic substance, using near-infrared spectral spectroscopy, so as to match the measured value according to the instrument for measuring a biogenic substance, using the confocal optical system, and (4) the step of executing an operation in the step (3) at least once after the elapse of predetermined time.

DETAILED DESCRIPTION OF EXEMPLARY EMBODIMENTS

Figure 1:
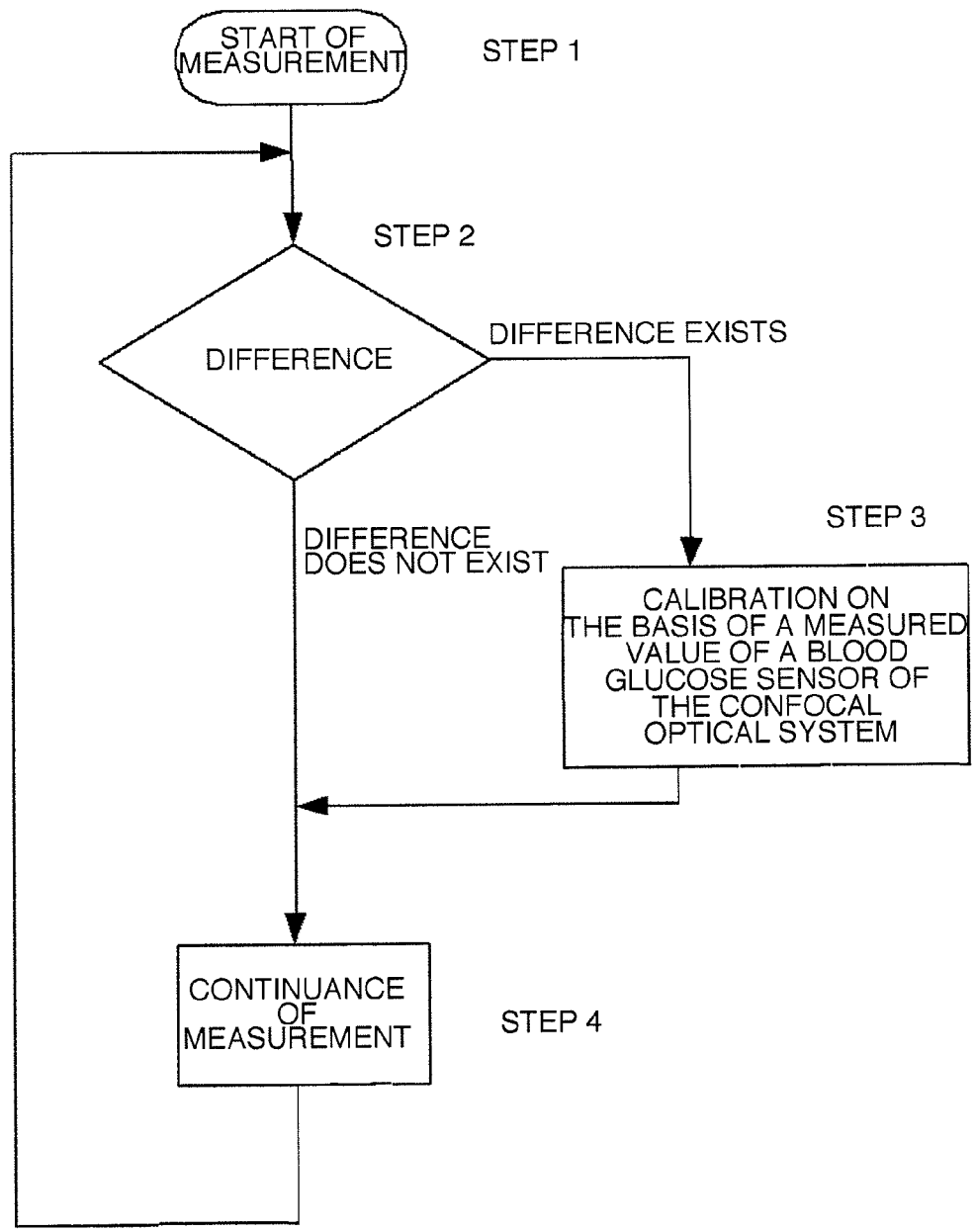
FIG. 1 is a flow chart showing an embodiment of a method for calibrating an instrument for measuring a biogenic substance, using near-infrared spectral spectroscopy, according to the invention, by way of example.
Figure 2:
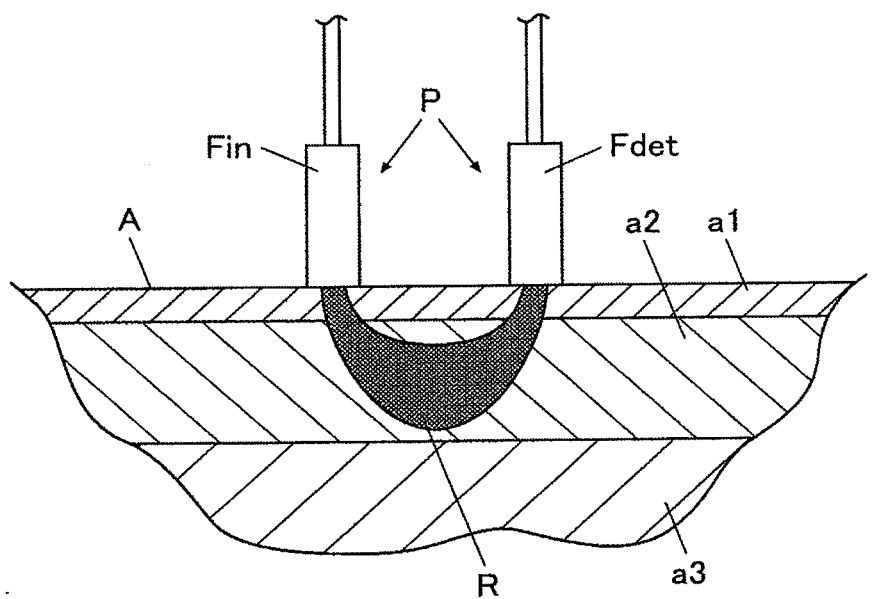
FIG. 2 is a schematic representation showing a measuring method with the use of an instrument for measuring a biogenic substance, using near-infrared spectral spectroscopy.

FIG. 1 is a flow chart showing non-infesting calibration of an instrument for measuring a biogenic substance, using near-infrared spectral spectroscopy, with the use of an instrument for measuring a biogenic substance, using a confocal optical system, as a reference.

Configurations of the respective instrument for measuring a biogenic substance are identical to that described with reference to the conventional example, omitting therefore description thereof.

Prior to the start of measurement in step 1, with the use of the respective instruments for measuring a biogenic substance, a value of a biogenic substance (for example, a blood glucose value) of a biological object of the same test subject is measured, and adjustment is made such that the respective values of the biogenic substance, measured by the respective instruments for measuring a biogenic substance, are in agreement with each other.

Further, adjustment is applied to at least one unit of the instrument for measuring a biogenic substance, using near-infrared spectral spectroscopy, against, for example, one unit of the instrument for measuring a biogenic substance, using the confocal optical system, and upon actual measurement, no measurement is carried out with the use of the instrument for measuring a biogenic substance, using the confocal optical system, since this instrument is for use as a reference. Measurement of, for example, a blood glucose value is carried out with the use of the instrument for measuring a biogenic substance, using near-infrared spectral spectroscopy.

With the elapse of predetermined time after the start of measurement in step 1, measurement of, for example, a blood glucose value of the test subject is carried out with the use of the instrument for measuring a biogenic substance, using the confocal optical system, in step 2, and a biological object of the same test subject is similarly measured with the use of the instrument for measuring a biogenic substance, using near-infrared spectral spectroscopy.

If a difference between respective measured values does not exist, the method proceeds to step 4 to continue measurement. If a difference between the respective measured values exists, the method proceeds to step 3, thereby calibrating the measured value obtained with the use of the instrument for measuring a biogenic substance, using near-infrared spectral spectroscopy so as to coincide with the measured value obtained with the use of the instrument for measuring a biogenic substance, using the confocal optical system.

Upon completion of calibration, the method proceeds to step 4 to continue measurement. Then, with the elapse of predetermined time, operation in the step 2 is repeated.

Further, time when the analytical curve of the instrument for measuring a biogenic substance, using near-infrared spectral spectroscopy, is deviated from a true value, is adopted as a guide for an interval in time for calibration by comparison of the instrument for measuring a biogenic substance, using the confocal optical system, with the instrument for measuring a biogenic substance, using near-infrared spectral spectroscopy, With the use of the method described as above, it is possible to implement non-infesting calibration of the instrument for measuring a biogenic substance, using near-infrared spectral spectroscopy, with the use of the instrument for measuring a biogenic substance, using the confocal optical system, as the reference.

Figure 3:
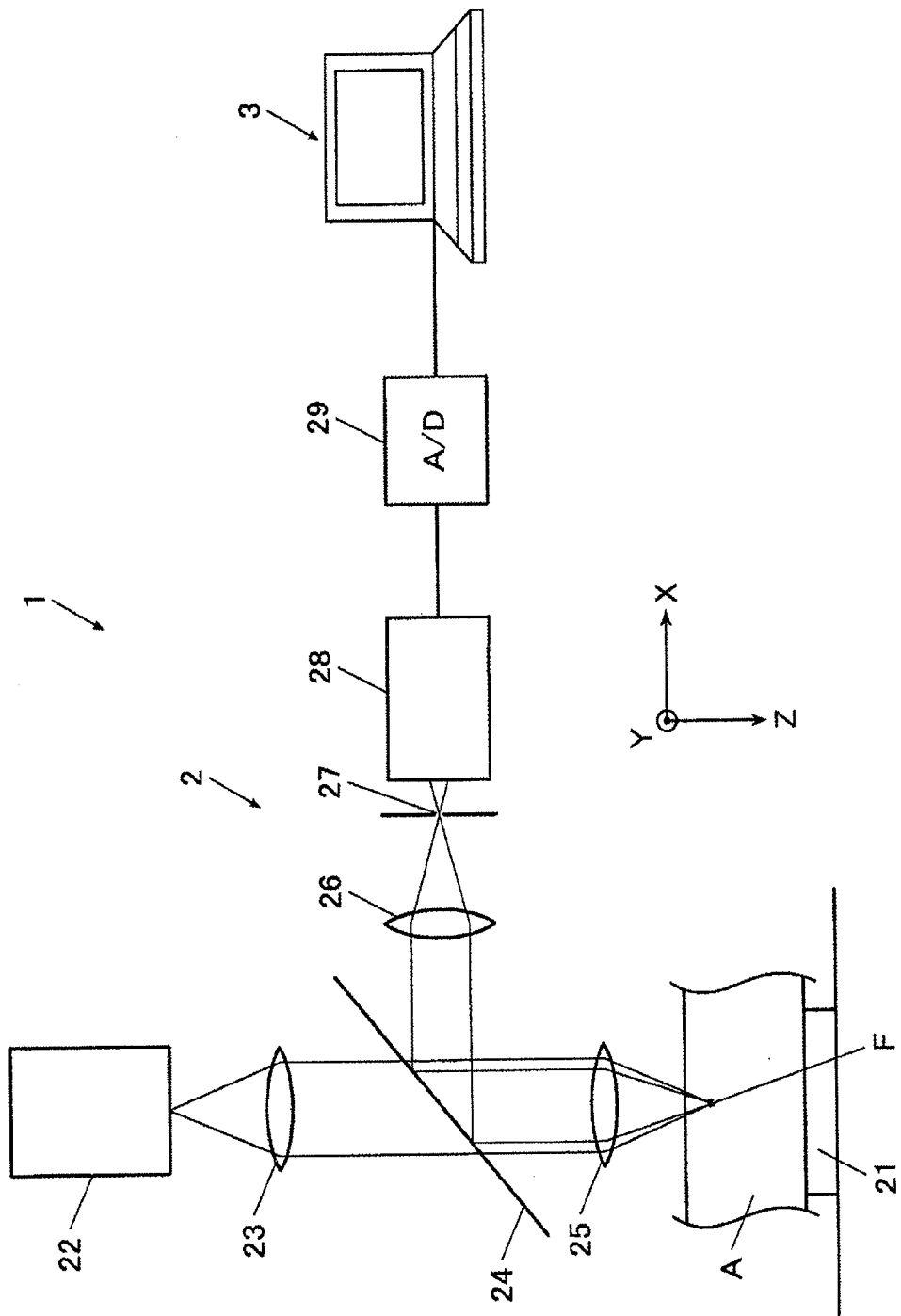
FIG. 3 is a block diagram of an instrument for measuring a biogenic substance, using a confocal optical system.
Figure 4:
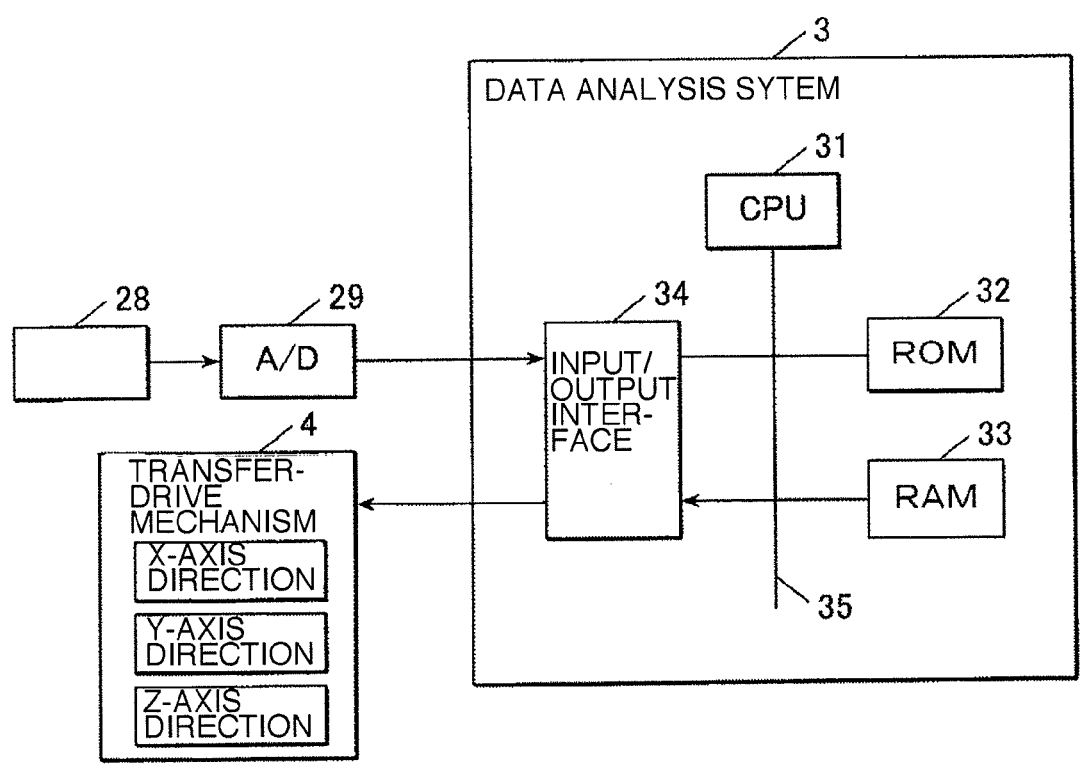
FIG. 4 is a block diagram of a data analysis system of the instrument for measuring a biogenic substance.
Figure 5:
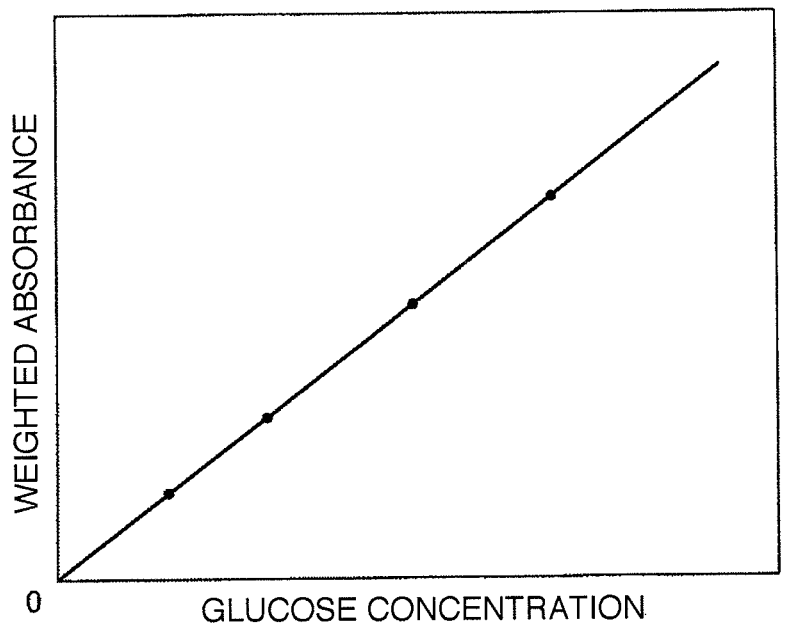
FIG. 5 is a graph showing an example of an analytical curve indicating a correlation between glucose concentration, and weighted absorbance.

Further, it is to be pointed out that the foregoing description shows a specific and preferred embodiment of the invention for illustrative purposes only. For example, each of the various lenses shown in FIG. 3 may be a combination of a plurality of lenses, and the configuration may not be limited to that shown in FIG. 3.

With the use of the instrument for measuring a biogenic substance, using near-infrared spectral spectroscopy, this instrument being less expensive, it is possible to secure precision equivalent to that of the instrument for measuring a biogenic substance, using the confocal optical system, and to implement a non-infesting and simple calibration method for calibrating the instrument for measuring a biogenic substance, using near-infrared spectral spectroscopy.

While the present invention has been shown and described with reference to certain exemplary embodiments thereof, other implementations are within the scope of the claims. It will be understood by those skilled in the art that various changes in form and details may be made therein without departing from the spirit and scope of the invention as defined by the appended claims.

What is claimed is:

1. A calibration method for calibrating an instrument for measuring a biogenic substance, using near-infrared spectral spectroscopy, the method comprising:
   (1) the step of measuring a specific substance of a biological object with the use of an instrument for measuring a biogenic substance, using a confocal optical system,
   (2) the step of using an instrument for measuring a biogenic substance, using near-infrared spectral spectroscopy, thereby measuring a specific substance in the same region of the biological object that is measured with the use of the instrument for measuring a biogenic substance, using the confocal optical system,
   (3) the step of comparing a measured value of the specific substance, measured in the step (1) with the use of the instrument for measuring a biogenic substance, using the confocal optical system, with a measured value of the specific substance, measured in the step (2) with the use of the instrument for measuring a biogenic substance, using near-infrared spectral spectroscopy, and calibrating the measured value of the specific substance, measured with the use of the instrument for measuring a biogenic substance, using near-infrared spectral spectroscopy, so as to match the measured value according to the instrument for measuring a biogenic substance, using the confocal optical system, and
   (4) the step of executing an operation in the step (3) at least once after the elapse of predetermined time.

2. The calibration method according to claim 1, wherein the specific substance of the biological object is a blood glucose value.

3. A calibration method for calibrating an instrument for measuring a biogenic substance, using near-infrared spectral spectroscopy, the method comprising:
   (1) the step of measuring a specific substance of a biological object with the use of an instrument for measuring a biogenic substance, using a confocal optical system,
   (2) the step of using an instrument for measuring a biogenic substance, using near-infrared spectral spectroscopy, thereby measuring a specific substance in the same region of the biological object that is measured with the use of the instrument for measuring a biogenic substance, using the confocal optical system,
   (3) the step of comparing a measured value of the specific substance, measured in the step (1) with the use of the instrument for measuring a biogenic substance, using the confocal optical system, with a measured value of the specific substance, measured in the step (2) with the use of the instrument for measuring a biogenic substance, using near-infrared spectral spectroscopy, and calibrating the measured value of the specific substance, measured with the use of the instrument for measuring a biogenic substance, using near-infrared spectral spectroscopy, so as to match the measured value according to the instrument for measuring a biogenic substance, using the confocal optical system, and
   (4) the step of executing an operation in the step (3) at least once after the elapse of predetermined time,
   wherein the predetermined time is determined based upon deviation of the measured value using near-infrared spectral spectroscopy from the measured value using the confocal optical system.

* * * * *